US012558162B2

(12) United States Patent

Wang

(10) Patent No.: US 12,558,162 B2

(45) Date of Patent: Feb. 24, 2026

(54) METHOD, SYSTEM AND APPARATUS FOR DESIGNING A BONE PLATE TO BE USED IN AN ORTHOPEDIC SURGERY

(71) Applicant: TAIWAN MAIN ORTHOPAEDIC BIOTECHNOLOGY CO., LTD., Taichung (TW)

(72) Inventor: Min-Liang Wang, Taichung (TW)

(73) Assignee: Taiwan Main Orthopaedic Biotechnology Co., Ltd., Taichung (TW)

( * ) Notice: Subject to any disclaimer, the term of this patent is extended or adjusted under 35 U.S.C. 154(b) by 1037 days.

(21) Appl. No.: 17/680,876

(22) Filed: Feb. 25, 2022

(65) Prior Publication Data

US 2023/0270499 A1 Aug. 31, 2023

(51) Int. Cl.
| | |
|---|---|
| *A61B 34/10* | (2016.01) |
| *A61B 34/00* | (2016.01) |
| *B33Y 50/00* | (2015.01) |
| *B33Y 80/00* | (2015.01) |
| *G06T 19/20* | (2011.01) |

(52) U.S. Cl.
CPC .............. *A61B 34/10* (2016.02); *A61B 34/25* (2016.02); *B33Y 50/00* (2014.12); *B33Y 80/00* (2014.12); *G06T 19/20* (2013.01); *A61B 2034/102* (2016.02); *A61B 2034/105* (2016.02); *A61B 2034/108* (2016.02); *G06T 2200/04* (2013.01); *G06T 2210/41* (2013.01)

(58) Field of Classification Search
CPC ... A61B 34/10; A61B 34/25; A61B 2034/108; A61B 2034/105; A61B 2034/102; G06T 19/20; G06T 2210/41; G06T 2200/04; B33Y 80/00; B33Y 50/00
See application file for complete search history.

(56) References Cited

U.S. PATENT DOCUMENTS

| | | | |
|---|---|---|---|
| 10,610,299 B2 | 4/2020 | Rueber et al. | |
| 2007/0276214 A1* | 11/2007 | Dachille ................ | G16H 30/40 |
| | | | 600/407 |
| 2014/0316561 A1* | 10/2014 | Tkachenko ............. | G07F 11/02 |
| | | | 700/236 |
| 2018/0147015 A1* | 5/2018 | She .......................... | G06T 5/70 |

FOREIGN PATENT DOCUMENTS

CA 3151349 A1 6/2015

OTHER PUBLICATIONS

Office Action issued to Indian counterpart application No. 202211013311 by the IPO on Apr. 24, 2025 (7 pages).

* cited by examiner

*Primary Examiner* — Sing-Wai Wu

(74) *Attorney, Agent, or Firm* — Osha Bergman Watanabe & Burton LLP

(57) ABSTRACT

A method for designing a bone plate to be used in an orthopedic surgery and to be placed on a bone structure includes: constructing a three-dimensional (3D) model of the bone structure; controlling a display screen to display an image that corresponds with the 3D model; in response to a plurality of designated points inputted on the image, calculating a plurality of sets of 3D coordinates respectively for the plurality of designated points, and generating an extension route based on the plurality of sets of 3D coordinates; and generating a 3D model of the bone plate based on the extension route and at least one pre-stored bone plate template.

14 Claims, 14 Drawing Sheets

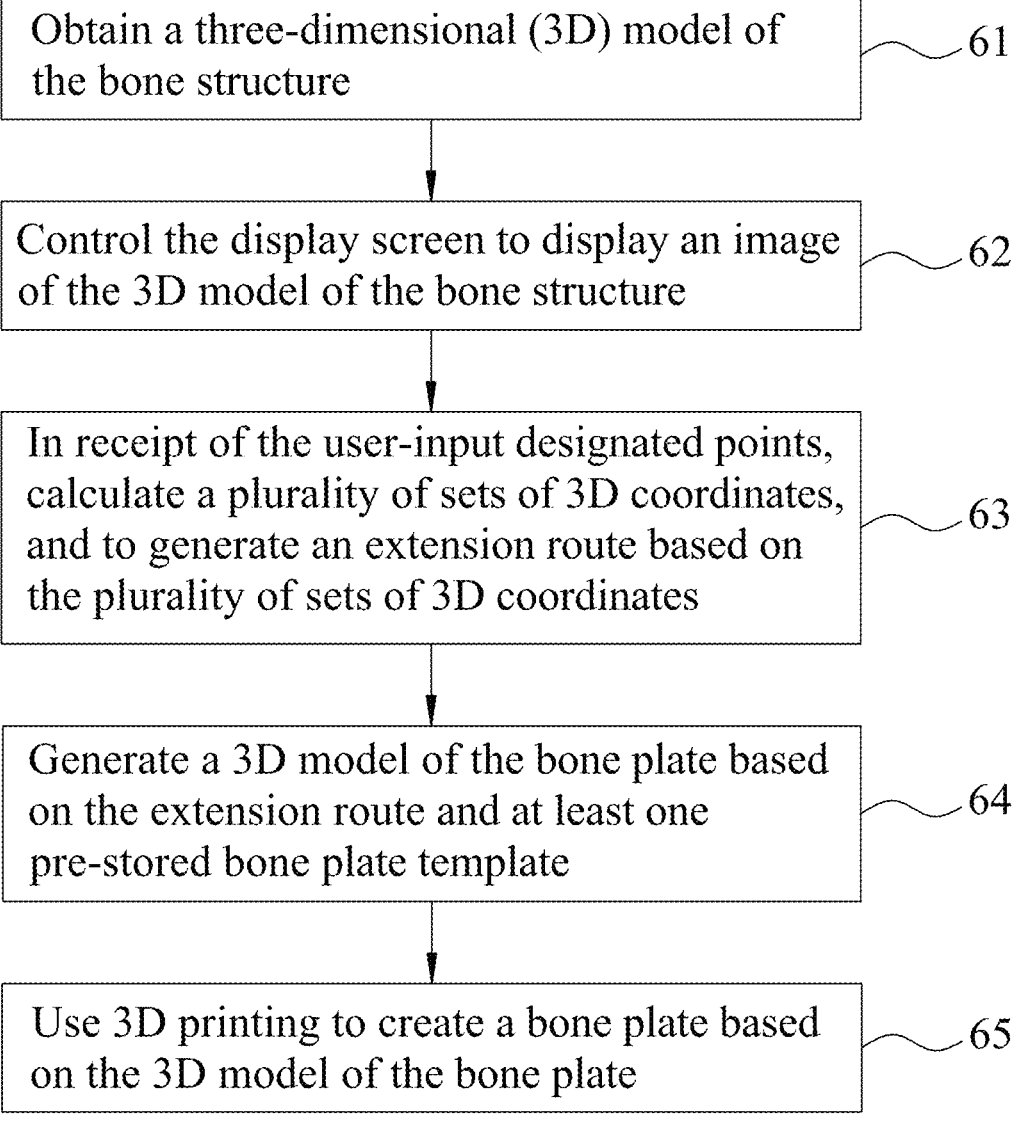

Obtain a three-dimensional (3D) model of the bone structure   ~61

Control the display screen to display an image of the 3D model of the bone structure   ~62

In receipt of the user-input designated points, calculate a plurality of sets of 3D coordinates, and to generate an extension route based on the plurality of sets of 3D coordinates   ~63

Generate a 3D model of the bone plate based on the extension route and at least one pre-stored bone plate template   ~64

Use 3D printing to create a bone plate based on the 3D model of the bone plate   ~65

METHOD, SYSTEM AND APPARATUS FOR DESIGNING A BONE PLATE TO BE USED IN AN ORTHOPEDIC SURGERY

FIELD

The disclosure relates to a method, a system and an apparatus for designing a bone plate to be used in an orthopedic surgery.

BACKGROUND

Orthopedics typically deals with patients that suffer from injuries related to the musculoskeletal system such as bone fractures, recurrent injuries, aging, etc. These conditions may cause one or more bones of a patient to be deformed or displaced from its/their original position(s). Most orthopedic surgeries involve planting a bone plate or a bone screw on a bone to make the bone and surrounding tissues stable, thereby achieving the result of allowing the bone to grow back in a preferred manner and/or moving the bone back to its original position.

It is noted that although a large number of bone plates with different specifications are commercially available, alterations (e.g., bending and/or cutting) may still be required on these commercially available bone plates to fit the actual shapes and sizes of various bones of musculoskeletal system of patients. This proves to be a time consuming process since the bone plates are typically made from metal materials such as stainless steel, alloys, etc.

SUMMARY

One object of the disclosure is to provide a method for designing a bone plate to be used in an orthopedic surgery.

According to one embodiment of the disclosure, the method is for designing a bone plate to be used in an orthopedic surgery, the bone plate is to be placed on a bone structure of a subject. The method is implemented using a system that includes a processor, a display screen and an interface. The method includes:

obtaining a three-dimensional (3D) model of the bone structure;

controlling the display screen to display an image that corresponds with the 3D model of the bone structure;

in response to user-input of a plurality of designated points on the image of the 3D model of the bone structure via the interface, calculating a plurality of sets of 3D coordinates respectively for the plurality of designated points in a 3D coordinate system of the 3D model of the bone structure;

generating an extension route based on the plurality of sets of 3D coordinates; and generating a 3D model of the bone plate based on the extension route and at least one pre-stored bone plate template.

Another object of the disclosure is to provide a system that is configured to implement the above-mentioned method.

According to one embodiment of the disclosure, the system for designing a bone plate is to be used in an orthopedic surgery. The bone plate to be placed on a bone structure of a subject. The system includes:

a data storage module that stores a three-dimensional (3D) model of the bone structure and a plurality of pre-stored bone plate templates therein; and a bone plate plotting module that is configured to in response to receipt of user-input of a plurality of designated points, calculate a plurality of sets of 3D coordinates respectively for the plurality of designated points in a 3D coordinate system of the 3D model of the bone structure, generate an extension route based on the plurality of sets of 3D coordinates, and generate a 3D model of a bone plate based on the extension route and at least one of the bone plate templates pre-stored in the data storage module.

Another object of the disclosure is to provide an apparatus that is configured to implement the above-mentioned method.

According to one embodiment of the disclosure, the apparatus is for designing a bone plate to be used in an orthopedic surgery, the bone plate to be placed on a bone structure of a subject, the apparatus comprising:

a rack;

a host disposed in the rack; and a touch panel connected to the rack and the host;

the host including a processor and a storage medium that stores a plurality of bone plate templates and a software application therein, the software application including instructions that, when executed by the processor, cause the processor to perform the operations of controlling the touch panel to display an image that corresponds with a 3D model of the bone structure, in response to user-input of a plurality of designated points on the image of the 3D model of the bone structure via the touch panel, calculating a plurality of sets of 3D coordinates respectively for the plurality of designated points in a 3D coordinate system of the 3D model of the bone structure, and generating an extension route based on the plurality of sets of 3D coordinates, and generating a 3D model of the bone plate based on the extension route and at least one of the bone plate templates.

BRIEF DESCRIPTION OF THE DRAWINGS

Other features and advantages of the disclosure will become apparent in the following detailed description of the embodiments with reference to the accompanying drawings, of which:

FIG. 3 is a flow chart illustrating steps of a method for designing a bone plate to be used in an orthopedic surgery according to one embodiment of the disclosure;

DETAILED DESCRIPTION

Figure 1:
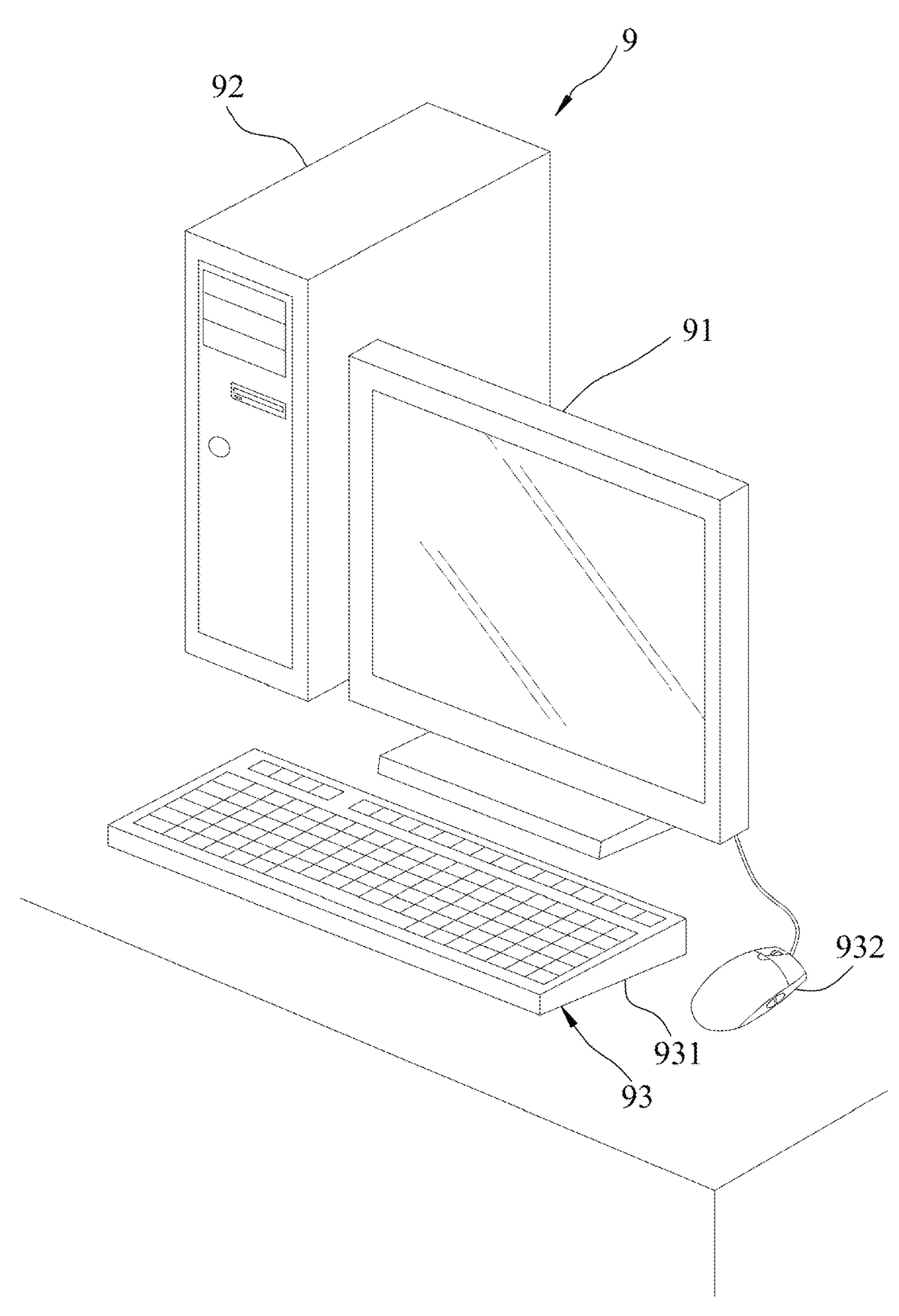
FIG. 1 is a schematic view of a computer system according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Throughout the disclosure, the term "coupled to" or "connected to" may refer to a direct connection among a plurality of electrical apparatus/devices/equipment via an electrically conductive material (e.g., an electrical wire), or an indirect connection between two electrical apparatus/devices/equipment via another one or more apparatus/devices/equipment, or wireless communication.

Figure 2:
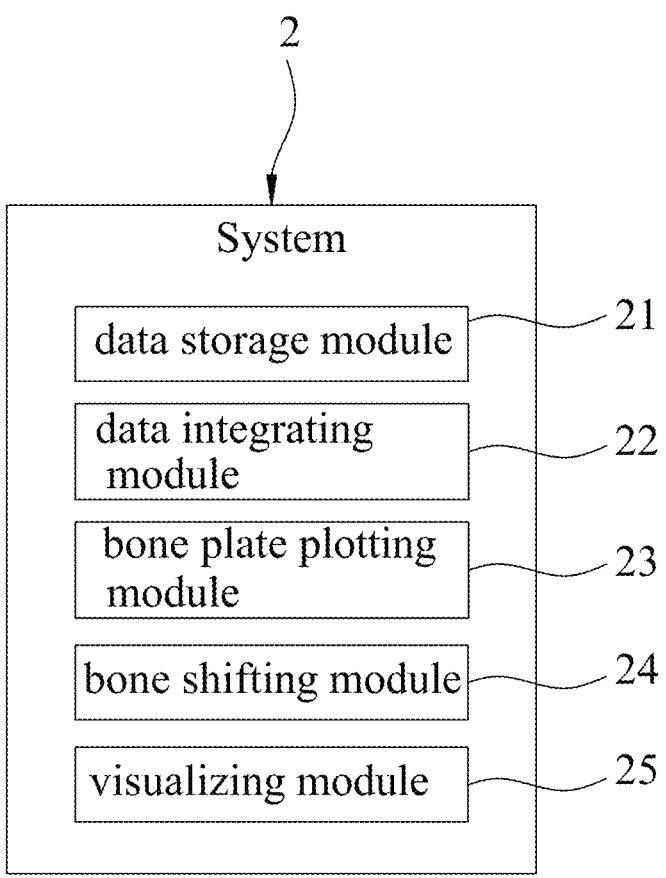
FIG. 2 is a block diagram of a system for designing a bone plate to be used in an orthopedic surgery according to one embodiment of the disclosure.

FIG. 2 is a block diagram of a system 2 for designing a bone plate to be used in an orthopedic surgery according to one embodiment of the disclosure. In this embodiment, the system 2 may be embodied using a computer system 9 as shown in FIG. 1. The computer system 9 may include a display screen 91, a host 92 and an interface 93.

The host 92 is connected to the display screen 91 and the interface 93, and may include a processor, a storage medium, a communication unit and other components (not depicted in the drawings) for embodying the functions of the system 2.

The processor may include, but not limited to, a single core processor, a multi-core processor, a dual-core mobile processor, a microprocessor, a microcontroller, a digital signal processor (DSP), a field-programmable gate array (FPGA), an application specific integrated circuit (ASIC), and/or a radio-frequency integrated circuit (RFIC), etc.

The communication unit may include at least one of a radio-frequency integrated circuit (RFIC), a short-range wireless communication module supporting a short-range wireless communication network using a wireless technology of Bluetooth® and/or Wi-Fi, etc., and a mobile communication module supporting telecommunication using Long-Term Evolution (LTE), the third generation (3G) and/or fifth generation (5G) of wireless mobile telecommunications technology, and/or the like.

The storage medium may be embodied using, for example, random access memory (RAM), read only memory (ROM), programmable ROM (PROM), firmware, flash memory, etc.

The interface 93 in this embodiment may include a keyboard 931 and a mouse 932, and may be connected to the host 92 in a wired manner or via wireless communication. In other embodiments, the interface 93 may include a touchscreen.

The system 2 includes a data storage module 21, a data integrating module 22, a bone plate plotting module 23, a bone shifting module 24 and a visualizing module 25.

In one example, the storage medium of the host 92 may store a software application therein. The software application includes instructions that, when executed by the processor, cause the processor to perform the functions of components of the system 2 (i.e., the data integrating module 22, the bone plate plotting module 23, the bone shifting module 24 and the visualizing module 25) as described below. In other embodiments, the host 92 may include firmware that includes instructions that, when executed by the processor, cause the processor to perform the functions of components of the system 2 as described below.

Figure 6:
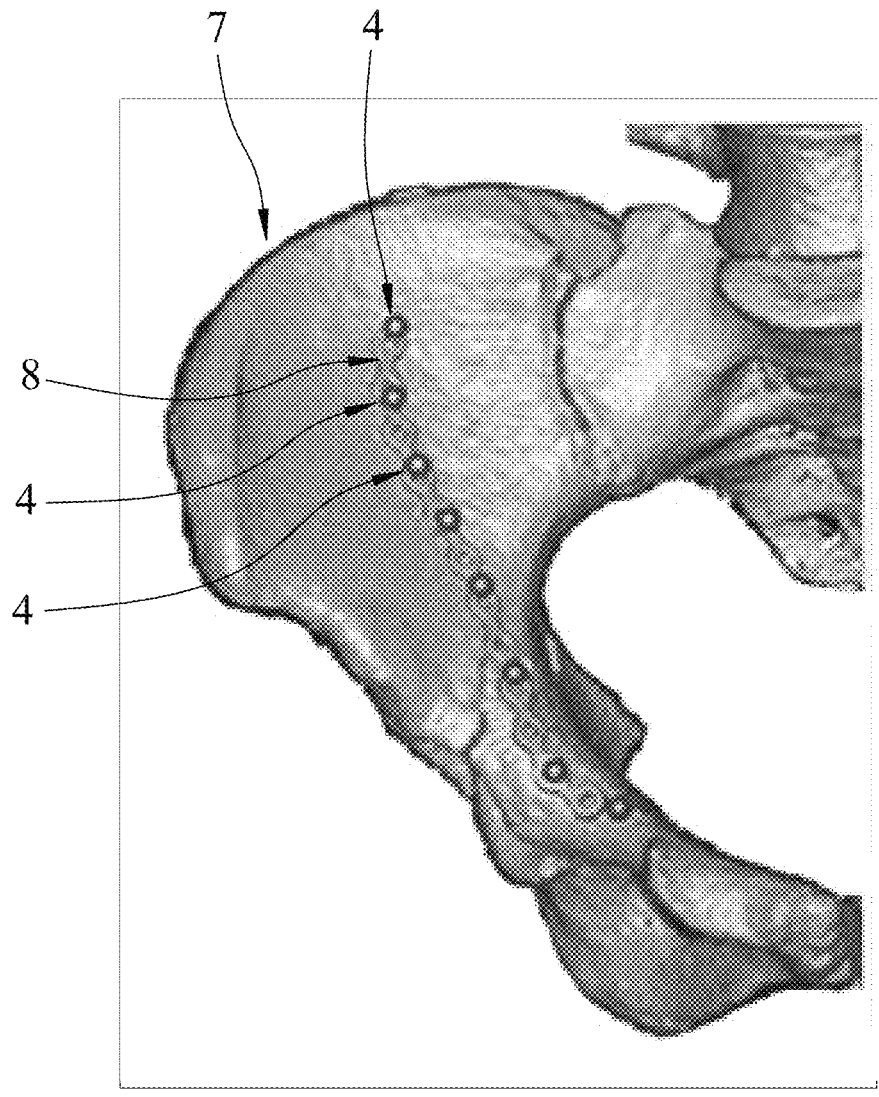
FIG. 6 illustrates a plurality of exemplary designated points and a bone plate on the image.

The data storage module 21 may be embodied using the storage medium of the host 92, and may store the software application and other data/information to be processed by the system 2. For example, the data storage module 21 may store a plurality of bone plate templates therein. One of the bone plate templates may be in the form of a chain plate which is a single piece cooperating with a plurality of the same chain plates to form a chain resembling a bicycle chain (as seen in FIG. 6), and other bone plate templates may be in other forms to be used in varying cases. For example, some bone plate templates may be composed with pre-designed shapes such as a square plate, a rectangular plate, a triangular plate, etc., with pre-determined dimensions and holes formed therein. The bone plate templates of different pre-designed shapes may be connected to generate other bone plate templates in order to fit the various needs.

The integrating module 22 is configured to, in response to receipt of a number of images of a bone structure, generate a three-dimensional (3D) model of the bone structure. The term "bone structure" throughout the disclosure may refer to one bone or a combination of a plurality of bones connected together. The bone structure may include one or more bones that are injured (such as suffering from bone fractures, recurrent injuries, aging, etc.), or have conditions that at least one bone of the bone structure is deformed or displaced from its original position. These conditions typically require an orthopedic surgery that utilizes a bone plate and/or bone screws to facilitate healing.

Specifically, in this embodiment, the images of the bone structure are two-dimensional (2D) images in the format of Digital Imaging and Communications in Medicine (DICOM), and the integrating module 22 is configured to extract the information contained in the images (e.g., distance information), and to generate the 3D model based on the images of the bone structure.

Figure 4:
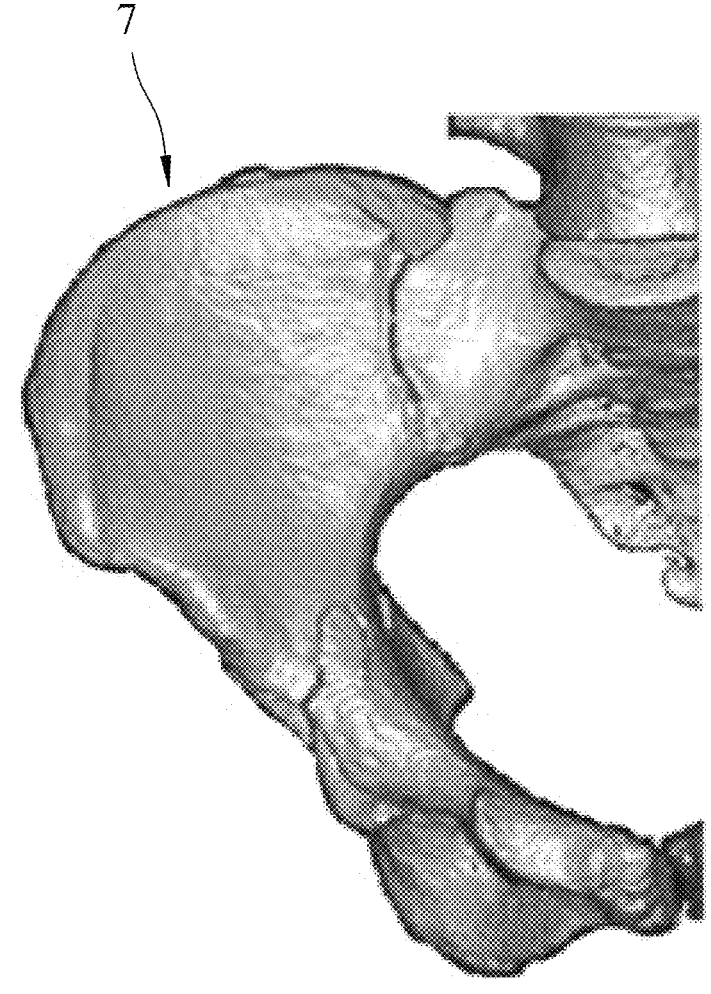
FIG. 4 illustrates an image of an exemplary 3D model of a bone structure generated by the system.

FIG. 4 illustrates an image of an exemplary 3D model of a bone structure 7 generated by the integrating module 22.

Figure 5:
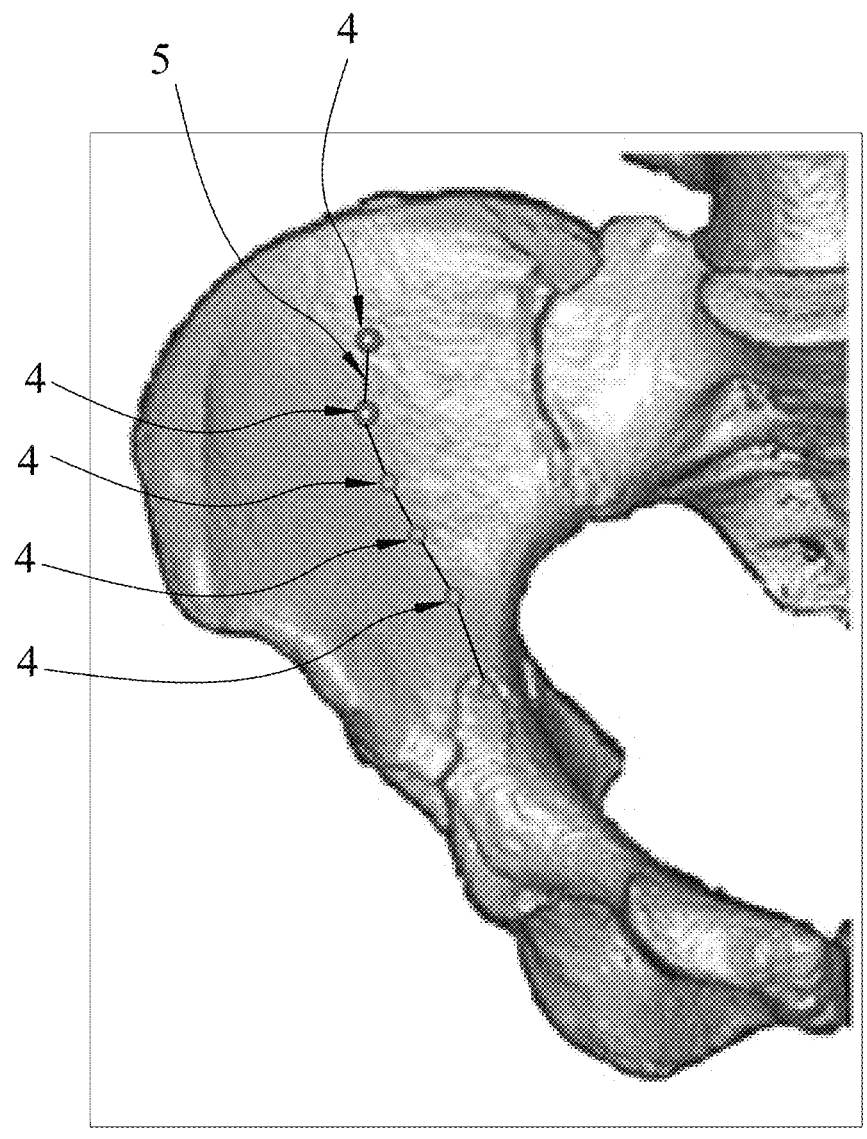
FIG. 5 illustrates exemplary designated points and a resulting extension route on the image.

The bone plate plotting module 23 is configured to, in response to receipt of user-input of a plurality of designated points 4 (see FIG. 5), calculate a plurality of sets of 3D coordinates respectively for the plurality of designated points 4 in a 3D coordinate system of the 3D model of the bone structure 7, and generate an extension route based on the plurality of sets of 3D coordinates (an exemplary extension route 5 passing through the designated points 4 is shown in FIG. 5). Then, the bone plate plotting module 23 is configured to generate a 3D model of a bone plate (an exemplary 3D model of a bone plate 8 shown in FIG. 6) based on the extension route and at least one of the bone plate templates pre-stored in the data storage module 21. In some cases, generation of a 3D model of a bone plate may only require two designated points.

The bone shifting module 24 is configured to, in response to receipt of a user input command to rotate, rotate the 3D model of the bone structure 7 and control the display screen 91 to display an altered image that corresponds with a rotated 3D model of the bone structure, and in response to receipt of a user input command to move, move the 3D model of the bone structure 7 and control the display screen 91 to display an altered image that corresponds with a moved 3D model of the bone structure.

The visualizing module 25 is configured to, in response to receipt of a user input command to divide, divide the 3D model of the bone structure 7 into the plurality of bone set and control the display screen 91 to display an altered image that corresponds with the plurality of bone sets. In the case that the bone structure includes a plurality of bones, the visualizing module 25 is configured to divide the plurality of bones in the 3D model of the bone structure 7 into a plurality of bone sets, and a number of bone(s) included in each of the bone sets is determined according to a separation parameter.

Figure 7:
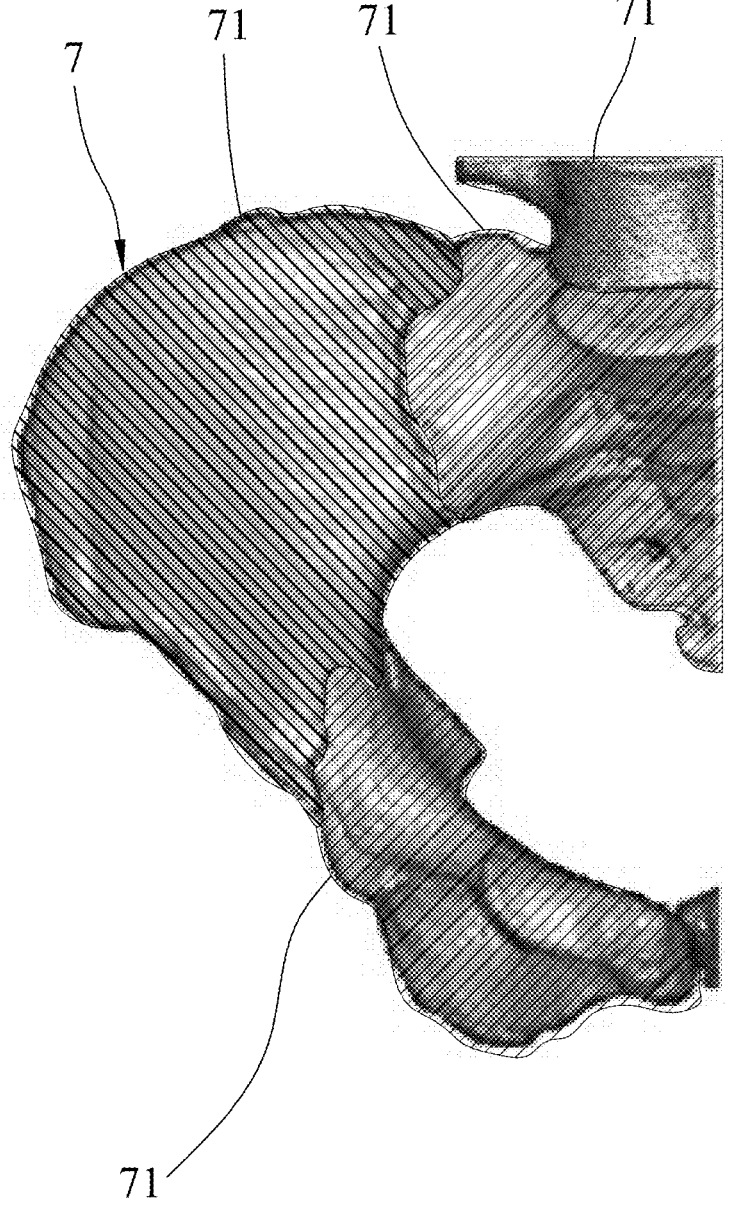
FIG. 7 illustrates an altered image that corresponds with the plurality of bone sets where the bone sets are labeled differently from each other.

Specifically, as shown in FIG. 7, the 3D model of the bone structure 7 may be divided into a plurality of bone sets 71, and each of the bone sets 71 may include one or several bones, the number of which is determined according to a separation parameter inputted via the interface 93.

Additionally, the visualizing module 25 is configured to control the display screen 91 to display the altered image that corresponds with the plurality of bone sets with the bone sets being marked in different manners, for example, by different colors or different patterns (as shown in FIG. 7).

In some embodiments, the visualizing module 25 is further configured to, in response to receipt of a further user input command to combine, combine user-selected two or more of the plurality of bone sets 71 to form a single bone set, and control the display screen 91 to display another altered image that corresponds with said single bone set (i.e., the user-selected two or more bone sets 71 that have been combined together). Additionally, the visualizing module 25 is configured to, in response to receipt of another user input command to further divide a user-selected one of the plurality of the bone sets 71, further divide the user-selected one of the plurality of the bone sets 71 into a plurality of smaller bone sets, and control the display screen 91 to display another altered image that corresponds with the plurality of the smaller bone sets, wherein the plurality of the smaller bone sets may be marked differently from each other.

FIG. 3 is a flow chart illustrating steps of a method for designing a bone plate to be used in an orthopedic surgery according to one embodiment of the disclosure. In this embodiment, the method is implemented using the computer system 9 as shown in FIG. 1. The host 92 of the computer system 9 may be pre-installed with the software application that enables the host 92 to perform the functions of the system 2, and is pre-stored with a number of bone plate templates.

In step 61, the host 92 obtains a three-dimensional (3D) model of the bone structure 7 (FIG. 4). Specifically, the operations of step 61 may include the user manually operating the interface 93 to import a plurality of 2D images of the bone structure into the host 92, which is configured to construct the 3D model of the bone structure 7. The 2D images may be computerized tomography (CT) scan images, or magnetic resonance imaging (MRI) images of the bone structure, and may be in the format of DICOM. In some cases, the 2D images may be contained in a single file folder and imported into the host 92 in batch.

Then, the host 92 constructs a 3D visualization using the 2D images, and determines the shape of the bone structure within the 3D visualization, so as to generate the 3D model of the bone structure 7. In use, the host 92 is configured to integrate the plurality of 2D images so as to generate the 3D model of the bone structure 7. Such operations may be done using existing software that are commercially available, and details thereof are omitted herein for the sake of brevity.

In some embodiments, the user may also operate the interface 93 to create one or more bone plate templates.

In step 62, the host 92 controls the display screen 91 to display an image of the 3D model of the bone structure 7 that corresponds with the 3D model of the bone structure 7.

At this stage, the user may be enabled to operate the interface 93 to "move" or "rotate" the 3D model of the bone structure 7, so as to view the image of the 3D model of the bone structure 7 on the display screen 91 in different angles or from different locations. In response to receipt of a first user input command to rotate the 3D model of the bone structure 7, the host 92 rotates the 3D model of the bone structure 7 and controls the display screen 91 to display an altered image that corresponds with the 3D model of the bone structure 7 which has been rotated according to the first user input command. For example, the first user input command includes a rotation direction and a rotation angle, instructing the host 92 of the direction in which and the angle by which to rotate the 3D model of the bone structure 7. In response to receipt of a second user input command to move the 3D model of the bone structure 7, the host 92 moves the 3D model of the bone structure 7 and controls the display screen to display an altered image that corresponds with the 3D model of the bone structure 7 which has been moved according to the second user input command. For example, the second user input command includes a moving direction and a moving distance, instructing the host 92 of the direction in which and the distance by which to move the 3D model of the bone structure 7.

In some embodiments, the user may be enabled to operate the interface 93 to perform additional actions such as zoom in, zoom out, etc., with respect to the 3D model of the bone structure 7 shown on the display screen 91.

In some embodiments, the user may be enabled to operate the interface 93 to "move" or "rotate" only a part of the 3D model of the bone structure 7. That is to say, the bone structure contained in the 3D model 7 may include a plurality of bones, and in some cases, only some of bones of the bone structure are injured and need to be dealt with. In use, the user may operate the interface 93 to input a user input command to divide the 3D model of the bone structure 7 into a plurality of bone sets, and a number of bone(s) included in each of the bone sets is determined according to a separation parameter. The separation parameter is a threshold value associated with a grayscale value and designated by the user in this embodiment, and may be other values, such as a default value, in other embodiments.

In the example of FIG. 7, the 3D model of the bone structure 7 is divided into a plurality of bone sets 71, and each of the bone sets 71 may include a number of bones which is determined according to the separation parameter inputted via the interface 93. Additionally, the visualizing module 25 is configured to control the display screen 91 to display an altered image that corresponds with the plurality of bone sets 71 wherein the plurality of bone sets are marked in different manners or applied with different colors, such that the user is able to easily distinguish the bone sets 71 from each other and identify the individual bone sets 71.

At this stage, the user may also be enabled to operate the interface 93 to input commands to merge two or more of the bone sets 71 to form one bone set 71, or to further divide one of the bone sets 71 into a plurality of bones or a plurality of smaller bone sets.

Such a function is provided for some cases where the bone(s) or surrounding tissues affected by the injury or the displacement are all within one of the bone sets 71, while the other bone sets 71 are healthy and do not require operation during the orthopedic surgery. In such cases, it may be beneficial to further divide the one of the bone sets 71, and to merge said the other bone sets 71 into a larger bone set, so as to render subsequent operations easier to be implemented.

Then, in step 63, the user operates the interface 93 to input a plurality of designated points 4 on the image of the 3D model of the bone structure 7 (see FIG. 5). In use, the user may operate the mouse 932 and click on various locations on the image of the 3D model of the bone structure 7 to input the designated points 4, or input the designated points 4 in other manners.

In receipt of the user-input designated points 4, the host 92 is configured to calculate a plurality of sets of 3D coordinates respectively for the plurality of designated points 4, and to generate an extension route 5 based on the plurality of sets of 3D coordinates. It is noted that the designated points 4 and the 3D model of the bone structure 7 share the same 3D coordinate system.

In this embodiment, the extension route 5 is generated by calculating, for every adjacent two of the designated points 4, a line connecting the adjacent two of the designated points 4, and then connecting the resulting lines to generate the extension route 5.

It is noted that in some embodiments, the host 92 is configured to plot the extension route 5 further according to a shape of the 3D model of the bone structure 7.

Specifically, as seen on FIG. 5, the bone of the bone structure on which the extension route 5 extends may have a surface that is crooked (e.g., have a concave or convex, or other non-flat surface). In such a case, it is beneficial to plot the extension route 5 to extend in a manner such that a curve of the extension route 5 fits a curve of the surface of the bone in the 3D coordinate system.

Then, in step 64, the host 92 is configured to generate a 3D model of the bone plate 8 based on the extension route 5 and at least one of the pre-stored bone plate templates. This step may be implemented in response to receipt of a user-input command via the interface 93 to generate the 3D model of the bone plate 8.

FIG. 6 illustrates a number of designated points 4 with the associated 3D model of the bone plate 8. In this embodiment, the designated points 4 are not aligned in a straight line, and therefore the extension route 5 is also not in a straight line, and may be further shaped based on the shape of the bone. As such, the resulting 3D model of the bone plate 8 may utilize the bone plate template that is in the form of a chain plate, and takes the form of a chain. That is to say, the 3D model of the bone plate 8 is generated by repeating the bone plate template having the form of a chain plate multiple times to form a chain that extends along the extension route 5.

Figure 14:
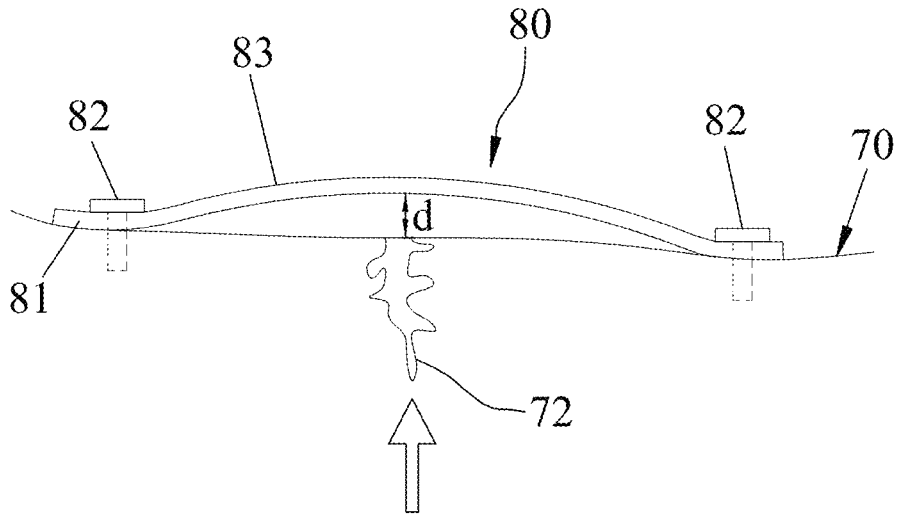
FIG. 14 illustrates an exemplary bone plate designed to accommodate a specific injury of a bone.

Referring to FIG. 14, in some embodiments, due to the nature of some of the bone-related injuries (e.g., a fracture 72), the bone plate 80 may be further shaped to accommodate the injury.

In one example shown in FIG. 14, the bone structure 70 has a fracture 72, and it is beneficial to form the bone plate 80 to have two end parts 81 and a bent portion 83 between the end parts 81. Each of the two end parts 81 may be formed with a through hole to allow a bone screw 82 to extend therethrough, so as to fasten the bone plate 80 onto the bone structure 70. The bent portion 83 has a shape such that, when the bone plate 80 is placed on the bone structure 70, the bent portion 83 has a largest distance (d) from the bone structure 70 that is no less than a predetermined distance. Typically, the largest distance (d) occurs between a middle part of the bone plate 80 and a location of the fracture 72.

This predetermined distance is kept so as to maintain a space between the bone structure 70 and the bone plate 80 for allowing the bone structure 70 and the surrounding tissues to heal and grow therein. Based on the severity of the injury, the predetermined distance may also be adjusted by the user operating the interface 93.

In the case that the bone structure 70 includes a hip bone and the fracture 72 is a moderate fracture (i.e., the overall shape of the bone is still intact), the predetermined distance may be set at about 3 millimeters to about 5 millimeters. On the other hand, in the case of a severe injury (such as comminuted open or compound fracture), the predetermined distance may be set at about 5 millimeters to about 10 millimeters. It is noted that for different bones and injuries, the predetermined distance may be adjusted.

As such, in the operations of generating the 3D model of the bone plate 8, an outer surface of the 3D model of the bone plate 8 may be shaped such that, when placed on the 3D model of the bone structure 7, a portion of the 3D model of the bone plate 8 that corresponds to the bent portion 83 has a largest distance from the 3D model of the bone structure 7 that is no less than the predetermined distance.

Then, in step 65, the host 92 is configured to use 3D printing to create a bone plate based on the 3D model of the bone plate 8.

Specifically, the host 92 may be controlled to establish a communication with a 3D printing equipment (not shown) with 3D printing functionalities, and to transmit the 3D model of the bone plate 8 to the 3D printing equipment so as to create the bone plate. In use, the bone plate may be created using a metal material (e.g., steel). In some embodiments, a number of bone screws to be used with the bone plate may also be created in this step.

It is noted that in some embodiments, an outer surface of the bone plate may be shaped such that, when placed on the bone structure, the bent portion of the bone plate has a largest distance from the bone structure that is no less than the predetermined distance.

As such, the bone plate that is custom-made for the specific bone structure and the specific injuries/conditions may then be used in the orthopedic surgery.

Figure 8:
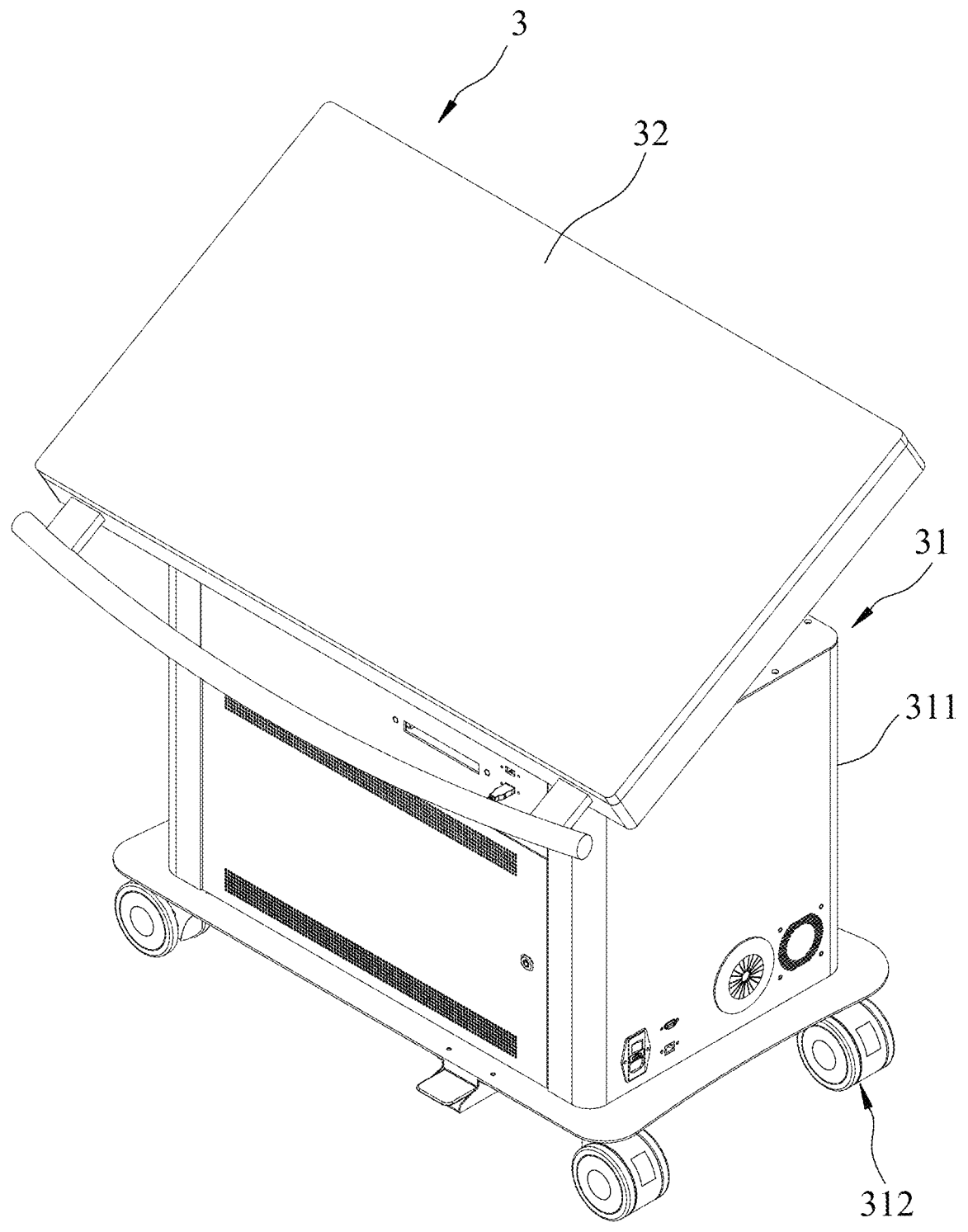
FIG. 8 is a perspective view of an apparatus for designing a bone plate to be used in an orthopedic surgery according to an embodiment of the disclosure.
Figure 9:
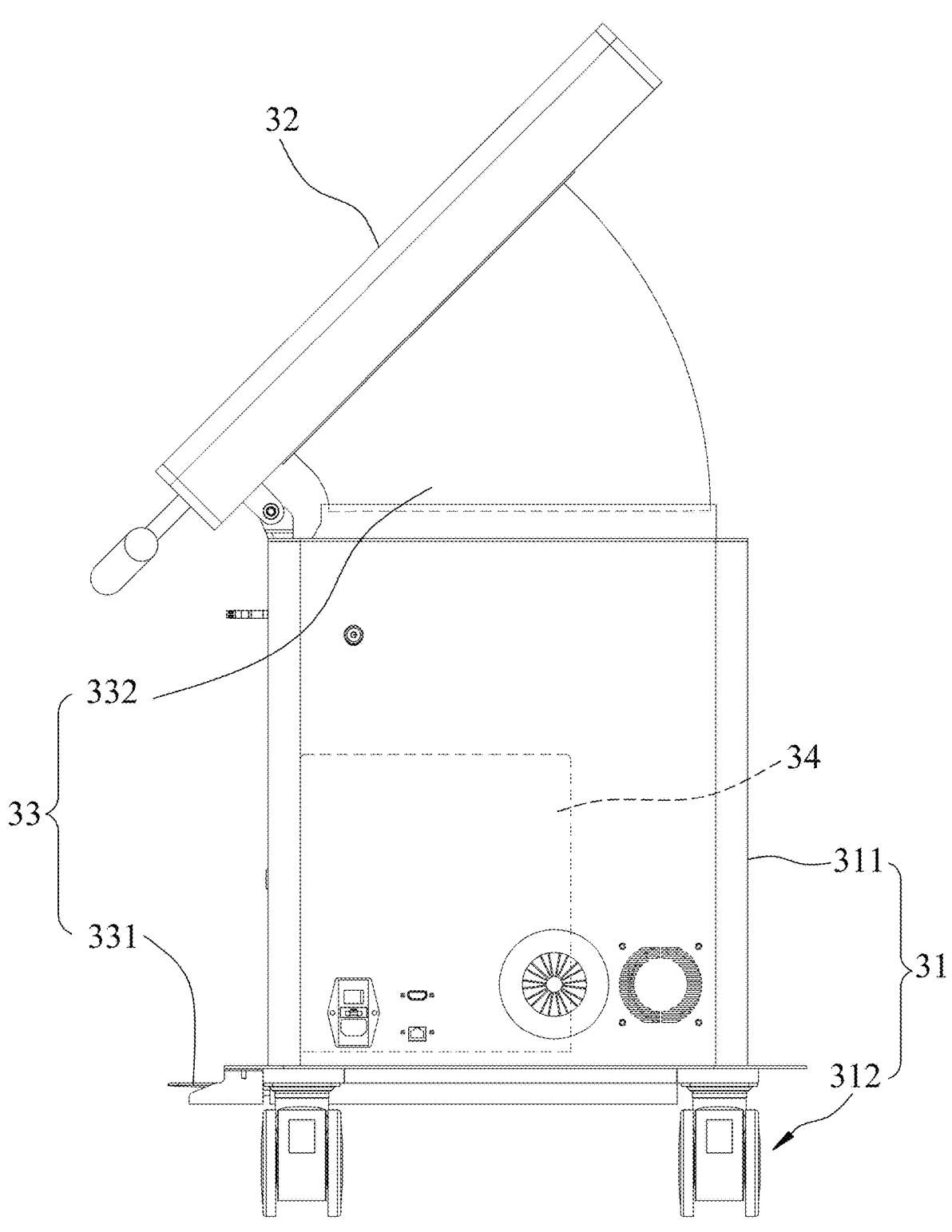
FIGS. 9 and 10 are side views of the apparatus of FIG. 8.
Figure 10:
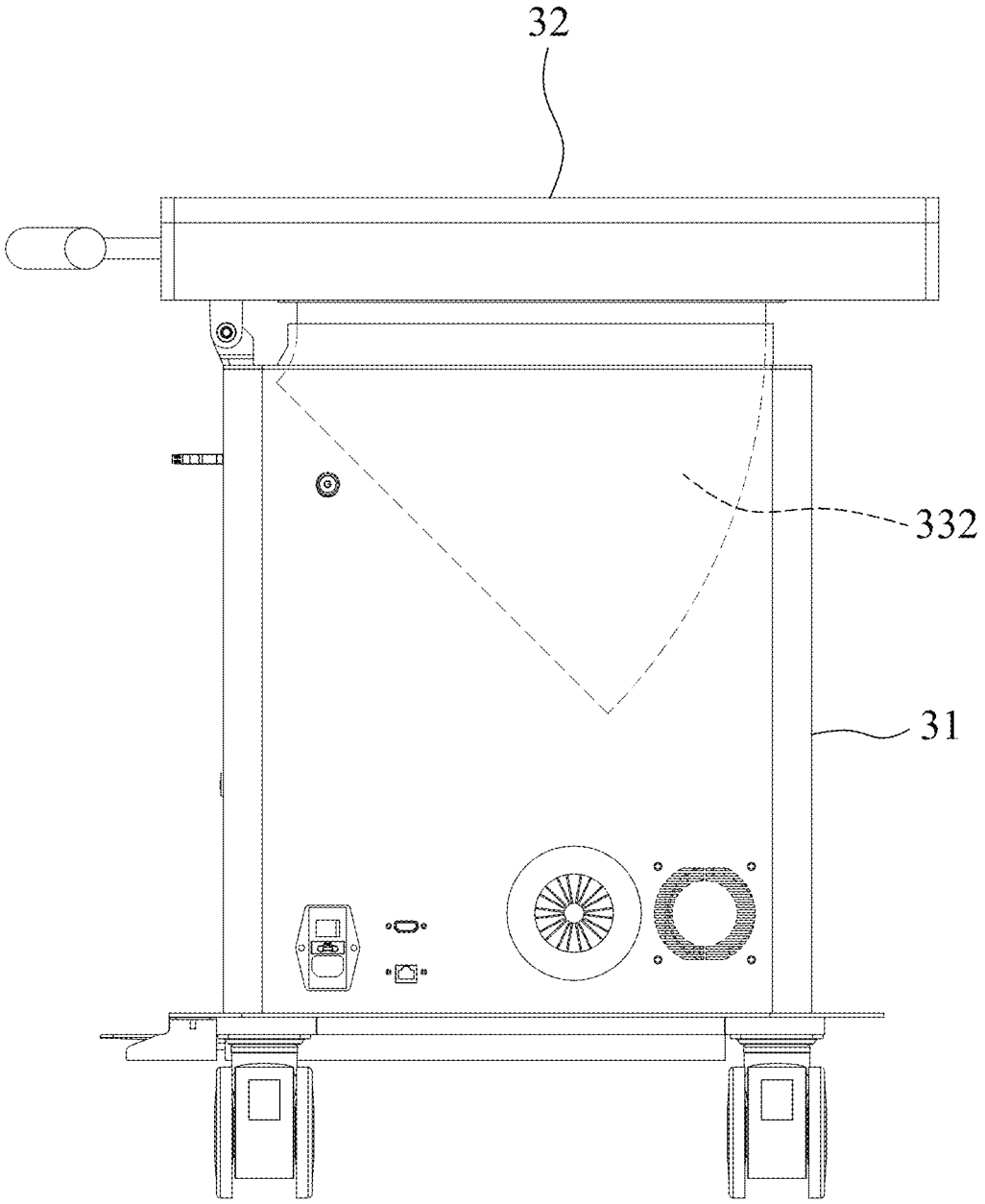

FIG. 8 is a perspective view of an apparatus 3 for designing a bone plate to be used in an orthopedic surgery according to one embodiment of the disclosure. FIGS. 9 and 10 are side views of the apparatus 3.

The apparatus 3 includes a rack 31, a touch panel 32, an actuating mechanism 33 and a host 34.

The rack 31 includes an outer shell 311 and a wheel set 312 (e.g., four wheels) disposed under the outer shell 311, allowing the apparatus 3 to be moved.

The touch panel 32 is hinged to the outer shell 311 of the rack 31, and may be switched between a lying position (as shown in FIG. 10) and a viewing position (as shown in FIG. 9). In this embodiment, the touch panel 32 may have a size that corresponds with a part of a human body (e.g., a height of about 80 to 100 centimeters, and a width of 50 to 80 centimeters).

The actuating mechanism 33 is connected to the rack 31 and the touch panel 32, and may be operated by a user to actuate the touch panel 32 to switch between the lying position and the viewing position.

In this embodiment, the actuating mechanism 33 includes a pedal 331 connected to the rack 31, at least one guiding board 332 having one end fixedly connected to the touch panel 32 and the other end movably connected to the rack 31, and an actuating member (not depicted in the drawings) connected to the touch panel 32.

The actuating member may be embodied using a pneumatic cylinder, a hydraulic cylinder or other actuating means, and operation thereof is restricted by the pedal 331 when the pedal 331 is not pressed. Specifically, movement of a piston rod is restricted by the pedal 331 when the pedal 331 is not pressed. In use, when a user steps on and presses the pedal 331, the pedal 331 releases the actuating member. As a result, the actuating member is configured to push the touch panel 32 upward, providing the force to move the touch panel 32 from the lying position to the viewing position. During movement of the touch panel 32, the guiding board 332 is used to guide and stabilize the movement of the touch panel 32.

On the other hand, in the viewing position, the user may directly push the touch panel 32 downward to move the touch panel 32 from the viewing position to the lying position.

The host 34 is disposed within the outer shell 311, is connected to the touch panel 32, and may be embodied using a host that is similar to the host 92 as described before. It is noted that the host 34 may also store the software application therein so as to perform the operations of the method of FIG. 3 and described above, and may store a plurality of bone plate templates therein.

In use, the user is enabled to move the apparatus 3 to an appropriate location by pushing the rack 31. Then, the user may step on the pedal 331 so as to move the touch panel 32 from the lying position to the viewing position. Then, the host 34 may be powered on, and the user may operate the touch panel 32, which serves as an interface having the function similar to that of the interface 93, to control the host 34 to execute the software application.

Then, the user may operate the touch panel 32 to control the host 34 to perform steps of the method of FIG. 3.

Specifically, in response to receipt of a plurality of 2D images of a bone structure, the host 34 is configured to construct a 3D model of the bone structure. In some embodiments, the 3D model of the bone structure may be pre-constructed using other devices (such as the host 92) and stored in a storage medium of the host 34.

Then, the host 34 is configured to control the touch panel 32 to display an image that corresponds with the 3D model of the bone structure.

In response to user-input of a plurality of designated points on the image of the bone structure via the touch panel 32, the host 34 is configured to calculate a plurality of sets of 3D coordinates respectively for the plurality of designated points in a 3D coordinate system of the 3D model of the bone structure, and to generate an extension route based on the plurality of sets of 3D coordinates. Then, the host 34 is configured to generate a 3D model of a bone plate based on the extension route and at least one of the bone plate templates stored in the host 34.

Figure 11:
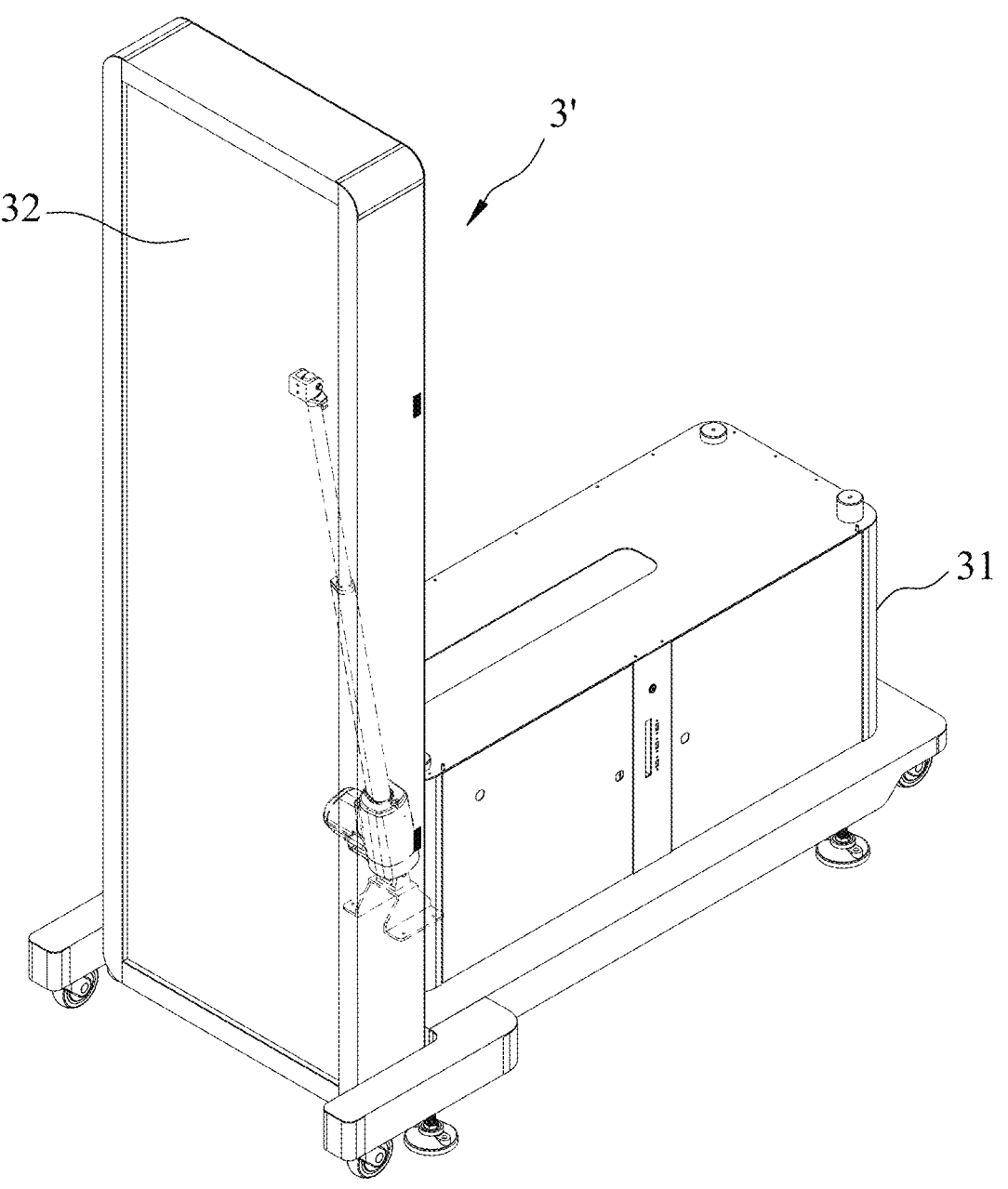
FIG. 11 is a perspective view of another apparatus for designing a bone plate to be used in an orthopedic surgery according to an embodiment of the disclosure.
Figure 12:
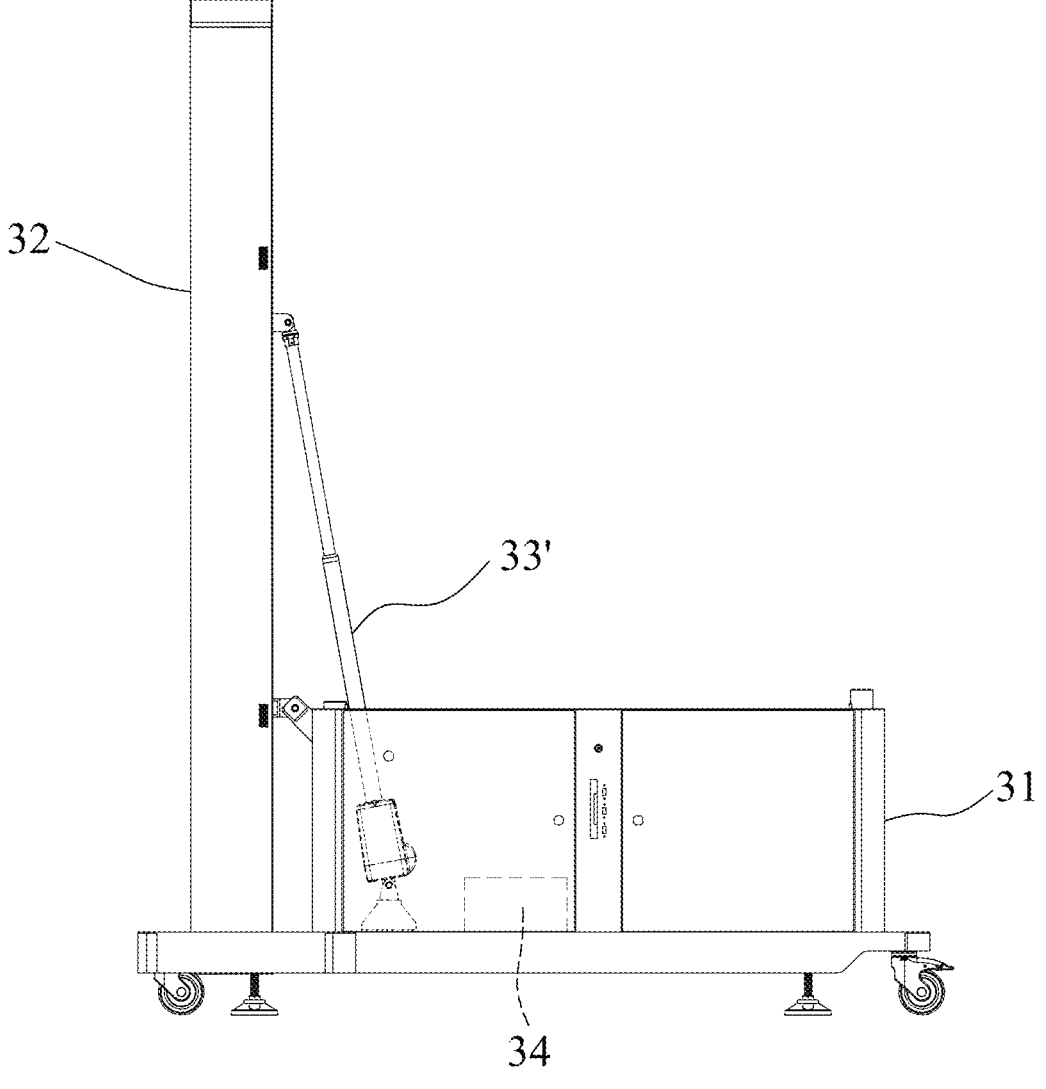
FIGS. 12 and 13 are side views of the apparatus of FIG. 11.
Figure 13:
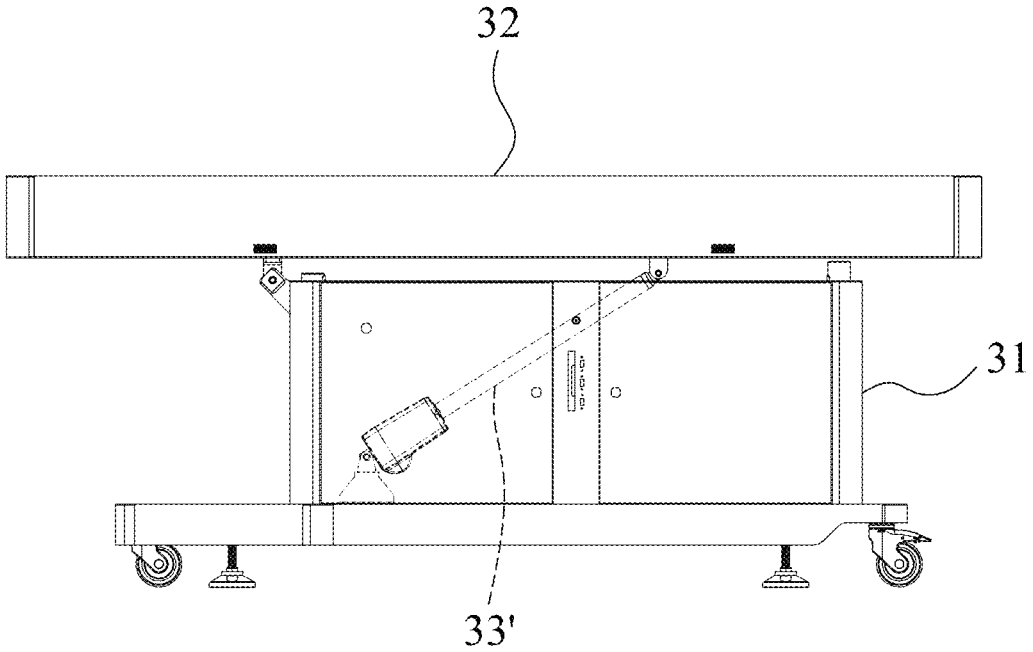

FIG. 11 is a perspective view of another apparatus 3' for designing a bone plate to be used in an orthopedic surgery according to one embodiment of the disclosure. FIGS. 12 and 13 are side views of the apparatus 3' of FIG. 11.

The apparatus 3' in this embodiment is similar to the apparatus 3 described in the embodiment of FIGS. 8 to 10, and differs therefrom in that the touch panel 32 of the apparatus 3' has a size that corresponds with the entire human body (e.g., a height of about 180 to 200 centimeters, and a width of 50 to 80 centimeters).

The apparatus 3' includes an actuating mechanism 33' that is different from the actuating mechanism 33 of the apparatus 3 and that is a retractable rod having one end hinged to a bottom surface of the touch panel 32 and another end hinged to the rack 31 of the apparatus 3'. The actuating mechanism 33' may be connected to the host 34 or a remote controller (not depicted in the drawings), and may be controlled by the remote controller to extend or to retract, so as to move the touch panel 32 between the lying position (as shown in FIG. 13) and the viewing position (as shown in FIG. 12).

In use, the user is enabled to move the apparatus 3' to an appropriate location by pushing the rack 31. Then, the user may operate the remote controller so as to move the touch panel 32 to move from the lying position to the viewing position. Then, the host 34 may be powered on, and the user may operate the touch panel 32 to control the host 34 to execute the software application.

Then, the user may operate the touch panel 32 to control the host 34 to perform steps of the method of FIG. 3.

To sum up, embodiments of the disclosure provide a method and a system for designing a bone plate to be used in an orthopedic surgery. In the method, a plurality of 2D images of a bone structure are utilized to generate a 3D model of the bone structure. Then, an image of the 3D model of the bone structure is displayed so as to enable a user to design a shape of the bone plate by manually inputting a plurality of designated points on the image. Then, a 3D model of a customized bone plate may be generated based on an extension route plotted from the designated points and a bone plate template. Such a bone plate may be more fitting to the condition of the specific patient compared to the commercially available bone plates.

In some embodiments, the bone plate may be designed to fit the shape of the bone structure. In some embodiments, based on the severity of the injury of the bone structure, the bone plate may be designed to have a bent portion. When placed on the bone structure, the bent portion has a largest distance from the bone structure that is no less than a predetermined distance, so as to maintain a space between the bone structure and the bone plate for allowing the bone structure and the surrounding tissues to heal and grow therein.

In some embodiments, the user is enabled to input a command based on a separation parameter to divide the bone structure into a plurality of bone sets, and to further merge some of the bone sets or to further divide one of the bone sets, which may render the designing of the bone plate more convenient.

Embodiments of the disclosure also provide a movable apparatus that is configured to perform the above-mentioned method.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for designing a bone plate to be used in an orthopedic surgery, the bone plate having a bent portion and to be placed on a bone structure of a subject, the method being implemented using a system that includes a processor, a display screen and an interface, and comprising:

obtaining a three-dimensional (3D) model of the bone structure;

controlling the display screen to display an image that corresponds with the 3D model of the bone structure;

in response to user-input of a plurality of designated points on the image of the 3D model of the bone structure via the interface, calculating a plurality of sets of 3D coordinates respectively for the plurality of designated points in a 3D coordinate system of the 3D model of the bone structure;

generating an extension route based on the plurality of sets of 3D coordinates; and generating a 3D model of the bone plate based on the extension route and at least one pre-stored bone plate template;

wherein the generating of the 3D model of the bone plate includes shaping an outer surface thereof such that, when placed on the 3D model of the bone structure, a portion of the 3D model of the bone plate that corresponds to the bent portion has a largest distance from the 3D model of the bone structure that is no less than a predetermined distance.

2. The method of claim 1, wherein the generating of the extension route includes plotting the extension route further according to a shape of the bone structure.

3. The method of claim 1, further comprising:

in response to receipt of a first user input command to rotate the 3D model of the bone structure, controlling the display screen to display an altered image corresponding with the 3D model of the bone structure that has been rotated according to the first user input command; and in response to receipt of a second user input command to move the 3D model of the bone structure, controlling the display screen to display an altered image corresponding with the 3D model of the bone structure that has been moved according to the second user command.

4. The method of claim 1, the bone structure including a plurality of bones, the method further comprising dividing the 3D model of the bone structure into a plurality of bone sets, each of the bone sets including a number of bones according to a separation parameter.

5. The method of claim 4, further comprising controlling the display screen to display an altered image that corresponds with the plurality of bone sets, wherein the plurality of bone sets are marked in different manners.

6. The method of claim 5, further comprising:

merging at least two of the plurality of bone sets to form one bone set, and controlling the display screen to display another altered image that corresponds with said one bone set.

7. The method of claim 6, further comprising:

further dividing one of the plurality of the bone sets into a plurality of smaller bone sets, and controlling the display screen to display another altered image that corresponds with the plurality of the smaller bone sets.

8. The method of claim 1, further comprising using 3D printing to create the bone plate based on the 3D model of the bone plate.

9. The method of claim 1, wherein the obtaining of the 3D model of the bone structure includes receiving a plurality of two-dimensional images of the bone structure, and integrating the plurality of two-dimensional images so as to generate the 3D model of the bone structure.

10. A system for designing a bone plate to be used in an orthopedic surgery, the bone plate having a bent portion and to be placed on a bone structure of a subject, the system comprising:

a host including a processor and a non-transitory computer readable storage medium that stores a three-dimensional (3D) model of the bone structure, a plurality of bone plate templates and a software application therein, the software application including a bone plate plotting module that, when executed by said processor, causes said processor to perform the operations of:

in response to receipt of user-input of a plurality of designated points, calculating a plurality of sets of 3D coordinates respectively for the plurality of designated points in a 3D coordinate system of the 3D model of the bone structure, generating an extension route based on the plurality of sets of 3D coordinates, and generating a 3D model of a bone plate based on the extension route and at least one of the bone plate templates pre-stored in said data storage module;

wherein the generating of the 3D model of the bone plate includes shaping an outer surface thereof such that, when placed on the 3D model of the bone structure, a portion of the 3D model of the bone plate that corresponds to the bent portion has a largest distance from the 3D model of the bone structure that is no less than a predetermined distance.

11. The system of claim 10, wherein said bone plate plotting module, when executed by said processor, further causes said processor to:

generate the extension route by plotting the extension route further according to a shape of the bone structure.

12. The system of claim 10, the bone structure includes including a plurality of bones, wherein a visualizing module that, when executed by said processor, causes said processor to perform the operations of:

in response to receipt of a user input command to divide the 3D model of the bone structure into the plurality of bone sets, dividing the plurality of bones into a plurality of bone sets, and a number of bone(s) included in each of the bone sets is determined according to a separation parameter;

in response to receipt of a further user input command, combining at least two of the plurality of bone sets to form one bone set; and in response to receipt of another user input command to divide one of the plurality of the bone sets, further dividing the one of the plurality of the bone sets into a plurality of smaller bone sets.

13. An apparatus for designing a bone plate to be used in an orthopedic surgery, the bone plate having a bent portion and to be placed on a bone structure of a subject, the apparatus comprising:

a rack;

a host disposed in said rack; and a touch panel connected to said rack and said host;

said host including a processor and a storage medium that stores a plurality of bone plate templates and a software application therein, the software application including instructions that, when executed by said processor, cause said processor to perform the operations of controlling said touch panel to display an image that corresponds with a 3D model of the bone structure, in response to user-input of a plurality of designated points on the image of the 3D model of the bone structure via said touch panel, calculating a plurality of sets of 3D coordinates respectively for the plurality of designated points in a 3D coordinate system of the 3D model of the bone structure, and generating an extension route based on the plurality of sets of 3D coordinates, and generating a 3D model of the bone plate based on the extension route and at least one of the bone plate templates;

wherein the generating of the 3D model of the bone plate includes shaping an outer surface thereof such that, when placed on the 3D model of the bone structure, a portion of the 3D model of the bone plate that corresponds to the bent portion has a largest distance from the 3D model of the bone structure that is no less than a predetermined distance.

14. The apparatus of claim 13, further comprising an actuating mechanism that is connected to said rack and said touch panel, said actuating mechanism being configured to move said touch panel from a lying position to a viewing position.

* * * * *